United States Patent
Qi

(10) Patent No.: US 10,669,352 B2
(45) Date of Patent: Jun. 2, 2020

(54) 6-DEOXY-6-THIOETHER-AMINO ACID CYCLODEXTRIN DERIVATIVE AND PREPARATION METHOD THEREOF

(71) Applicant: Hangzhou Adamerck Pharmlabs Inc., Hangzhou (CN)

(72) Inventor: Youmao Qi, Hangzhou (CN)

(73) Assignee: Hangzhou Adamerck Pharmlabs Inc., Hangzhou, Zhejiang ( * ) Notice: Subject to any disclaimer, the term of this patent is extended or adjusted under 35 U.S.C. 154(b) by 0 days.

(21) Appl. No.: 16/028,902

(22) Filed: Jul. 6, 2018

(65) Prior Publication Data

US 2019/0010255 A1  Jan. 10, 2019

Related U.S. Application Data

(62) Division of application No. 13/989,794, filed as application No. PCT/CN2011/082577 on Nov. 21, 2011, now Pat. No. 10,017,584.

(30) Foreign Application Priority Data

Nov. 26, 2010 (CN) .......................... 2010 1 0566606

(51) Int. Cl.
*C08B 37/16* (2006.01)
*A61K 31/724* (2006.01)
*A61K 47/40* (2006.01)

(52) U.S. Cl.
CPC ........ *C08B 37/0012* (2013.01); *A61K 31/724* (2013.01); *A61K 47/40* (2013.01)

(58) Field of Classification Search
None
See application file for complete search history.

(56) References Cited

U.S. PATENT DOCUMENTS

| | | | |
|---|---|---|---|
| 6,080,733 | A | 6/2000 | Defaye |
| 10,017,584 | B2 | 7/2018 | Qi |
| 2005/0153932 | A1 | 7/2005 | Sprengers et al. |
| 2006/0210527 | A1 | 9/2006 | Davis |
| 2009/0023210 | A1 | 1/2009 | Karginov et al. |
| 2013/0244979 | A1 | 9/2013 | Qi |

FOREIGN PATENT DOCUMENTS

| | | |
|---|---|---|
| CN | 1402737 | 3/2003 |
| CN | 1188428 | 2/2005 |
| CN | 101235104 | 8/2008 |
| CN | 101591402 | 12/2009 |
| CN | 101864003 | 10/2010 |
| CN | 102060941 | 5/2011 |
| FR | 2861396 | 4/2005 |
| JP | 4309502 | 2/1992 |
| JP | 2007-538112 | 12/2007 |
| WO | WO 2006/001844 | 1/2006 |
| WO | WO 2007/072481 | 6/2007 |

OTHER PUBLICATIONS

Donati, F., Expert Opinion on PHarmacotherapy, "Sugammadex: a cyclodextrin to reverse neuromuscular blockade in anaesthesia", 2008, vol. 9, No. 8, pp. 1375-1386 (Year: 2008).*
Ashton et al., "Amino Acid Derivatives of Beta-Cyclodextrin," The Journal of Organic Chemistry 61(3):903-908, Feb. 1996.
Atkuri et al., "N-Acetylcysteine—a safe antidote for cysteine/glutathione deficiency," Current Opinion in Pharmacology 7(4):355-359, Aug. 2007.
English machine translation of CN 101864003 A; Google translate; obtained Dec. 11, 2015; 6 pages.
International Preliminary Report on Patentability in Application No. PCT/CN2011/082577, dated May 28, 2013, 10 pages (English Translation).
International Search Report and Written Opinion in Application No. PCT/CN2011/082577, dated Mar. 1, 2012, 14 pages (English Translation).
European Search Report in Appln. No. PCT/CN2011/082577, dated May 8, 2014, 4 pages.

* cited by examiner

Primary Examiner — Shaojia A Jiang
Assistant Examiner — Bahar Craigo
(74) Attorney, Agent, or Firm — Fish & Richardson P.C.

(57) ABSTRACT

6-deoxy-6-thioether-amino acid cyclodextrin derivative is obtained by condensing an amino acid derivative with halogenated cyclodextrin in presence of alkali. The 6-deoxy-6-thioether-amino acid cyclodextrin derivative includes 6-deoxysulfinyl-6-thioether-amino acid cyclodextrin derivative and 6-deoxysulfonyl-6-thioether-amino acid cyclodextrin derivative. Compounds provided are for reversing neuromuscular relaxation in patients and animals induced by muscular relaxants. The compounds are able to rapidly reverse and antagonize muscular relaxation induced by muscular relaxants and can be administrated in preparing a drug having an antagonist effect on muscular relaxation. The compounds have low production cost and are able to reverse and antagonize a wide rage of muscular relaxations, thus effectively broaden scope of clinical use. More importantly, the compounds have a safe dose at least doubled compared to prior arts. The compounds have a general formula (I).

8 Claims, No Drawings

6-DEOXY-6-THIOETHER-AMINO ACID CYCLODEXTRIN DERIVATIVE AND PREPARATION METHOD THEREOF

CROSS REFERENCE OF RELATED APPLICATIONS

This application is a divisional of U.S. Serial No. 13/989,794, filed May 25, 2013, which is incorporated herein by reference in its entirety, which is a 35 U.S.C. § 371 National Stage Application of International Application PCT/CN2011/082577, filed November 21, 2001, which claims the benefit of priority to Chinese application CN 201010566606.3, filed Nov. 26, 2010.

BACKGROUND OF THE PRESENT INVENTION

Field of Invention

The present invention relates to a chemical pharmaceutical field, and more particularly to a 6-deoxy-6-thioether-amino acid cyclodextrin derivative and a preparation method thereof, mainly comprising a 6-deoxysulfinyl-6-thioether-amino acid cyclodextrin derivative, a 6-deoxysulfonyl-6-thioether-amino acid cyclodextrin derivative, preparation methods thereof, and a method for antagonizing muscular relaxation comprising administrating a drug comprising a therapeutically effective amount of the 6-deoxy-6-thioether-amino acid cyclodextrin derivative, wherein the drug is able to rapidly reverse the muscular relaxation induced by muscular relaxant and have features of high pharmaceutical security, available reactants and low cost.

Description of Related Arts

In 1986, it was reported on J.A.C.S. that (o-carboxyphenyl)thio cyclodextrin was synthesized by Tubashi. I.; in 1995, it was reported that carboxymethylthio cyclodextrin was synthesized by Guillo. F.; and in 1996, Baer. H. H. and Santoyo-Gonzalez. F. prepared 2,3-dihydroxypropylthio cyclodextrin having a following structural formula.

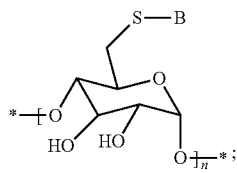

B = HOOCCH$_2$; PhCOOH; HOCH$_2$(HO)CHCH$_2$

A Chinese patent application, CN1402737, disclosed a preparation method of a similar compound having a following chemical structural formula (A):

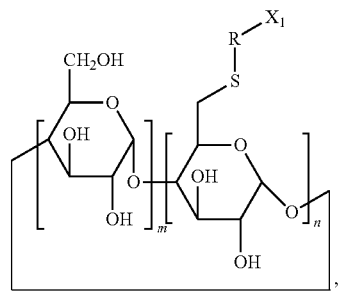

(A)

wherein m is one member selected from a group consisting of 0, 1, 2, 3, 4, 5, 6 and 7; n is one member selected from a group consisting of 1, 2, 3, 4, 5, 6, 7 and 8; a sum of m and n is 7 or 8;

R is (C$_1$-C$_6$)alkylene, optionally substituted with 1-3 OH groups or (CH$_2$)$_r$-phenylene-(CH$_2$)$_t$—, wherein r and t are independently 0-4; and X$_1$ is one member selected from a group consisting of COOH, CONHR$_6$, NHCOR$_7$, SO$_2$OH, PO(OH)$_2$, O(CH$_2$—CH$_2$—O)$_u$—H, OH and tetrazol-5-yl; R$_6$ is H or (C$_{1-3}$)alkyl; R$_7$ is carboxyphenyl; u is 1-3.

The compound mentioned above excludes substitutes having structures of amino acids.

Sugammadex is a species of 6-thioether cyclodextrin derivative disclosed in a Chinese patent application CN1402737. In July 2007, sugammadex (Bridion) of Schering Plough Company came into the market. The sugammadex is for reversing effects of rocuronium bromide and vecuronium bromide which are generally used as neuromuscular blocking drugs. The sugammadex is able to readily reverse the effects of the rocuronium bromide used for adults and generally reverse the effects of the vecuronium bromide used for children and teenagers between 2 and 17 years old.

However, the sugammadex has a main advantage of mere capability to antagonize the antagonist effect on the muscular relaxation induced by the rocuronium bromide and the vecuronium bromide, while having poor reversal or antagonism performance against other common muscular relaxants, such as pancuronium bromide, pipecuronium bromide, dacuronium bromide and quindonium bromide.

A Chinese patent application CN101591402 disclosed a structure (B) of 6-deoxy thioether amino acid cyclodextrin derivative and a preparation method thereof, wherein the preparation method thereof comprises firstly synthesizing halogenated cyclodextrin and then condensing mercapto compound with the halogenated cyclodextrin in presence of alkali, so as to obtain the 6-deoxy thioether amino acid cyclodextrin derivative.

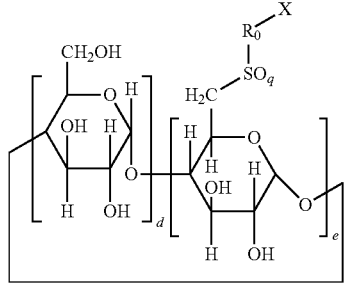

Structure (B)

In the structure (B), d is one member selected from a group consisting of 0, 1, 2, 3, 4, 5, 6, 7 and 8; e is one member selected from a group consisting of 1, 2, 3, 4, 5, 6, 7, 8 and 9; a sum of d and e is one member selected from a group consisting of 6, 7, 8 and 9;

q is 1 or 2;

R$_0$ is (C$_1$-C$_6$)alkylene, optionally substituted by 1-3 OH groups or (CH$_2$)x-phenylene-(CH$_2$)$_g$—, wherein x is one member selected from a group consisting of 0, 1, 2, 3 and 4 and g is one member selected from a group consisting of 0, 1, 2, 3 and 4; and X is one member selected from a group consisting of COOH, CONHR$_8$, NHCOR$_9$, SO$_2$OH, PO(OH)$_2$, O(CH$_2$—

CH$_2$—O)$_h$—H, OH and tetrazol-5-yl, wherein R$_8$ is H, (C$_{1-3}$)alkyl or (C$_{1-3}$)alkyl containing COOH; R$_9$ is carboxyphenyl; and h is 1, 2 or 3.

Disclosed by the Chinese patent application CN101591402, a method for antagonizing muscular relaxation comprising administrating a drug comprising a therapeutically effective amount of a compound is able to reverse the muscular relaxation induced by human or animal muscular relaxants and has reversal and antagonism effects on the muscular relaxation induced by the muscular relaxants.

The compound of the Chinese patent application CN101591402 has improved selectivity, but excludes substitutes having structures of α-position amino acids and derivatives thereof.

SUMMARY OF THE PRESENT INVENTION

An object of the present invention is to provide a 6-deoxy-6-thioether-amino acid cyclodextrin derivative of formula (I).

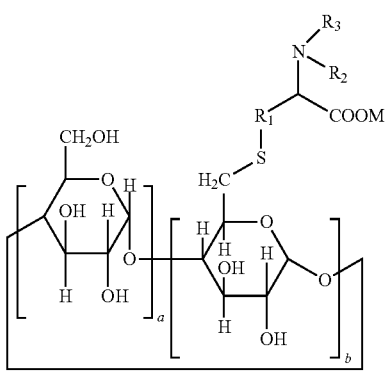

(II)

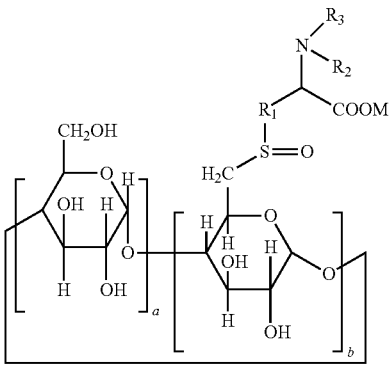

(III)

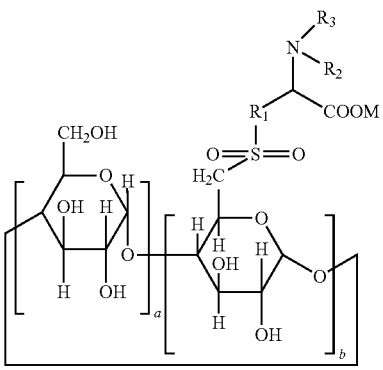

(IV)

In the formula (I), a is one member selected from a group consisting of 0, 1, 2, 3, 4, 5, 6, 7 and 8;

b is one member selected from a group consisting of 1, 2, 3, 4, 5, 6, 7, 8 and 9;

a sum of a and b is one member selected from a group consisting of 6, 7, 8 and 9;

f is 0, 1 or 2;

R$_1$ is (C$_1$-C$_6$)alkylene, optionally substituted by 1-2 CH$_3$ groups, 1-2 OH groups or (CH$_2$)$_v$-phenylene-(CH$_2$)$_k$—, wherein v is one member selected from a group consisting of 0, 1, 2, 3 and 4 and k is one member selected from a group consisting of 0, 1, 2, 3 and 4;

either of R$_2$ and R$_3$ is one member of D configuration, L configuration or racemic configuration selected from a group consisting of —H, formyl group, acetyl group, methyl group, ethyl group, carboxybenzyl (Cbz) group, tert-butoxycarboonyl (t-Boc) group, fluorenylmethoxycarbonyl, —CH$_2$COOM and hydroxyphenyl, wherein R$_2$ and R$_3$ have identical or different substituent groups; and M is —H, NH$_4$ or alkali metal ion.

When f is 0, the 6-deoxy-6-thioether-amino acid cyclodextrin derivative has a structure of formula (II);

when f is 1, the 6-deoxy-6-thioether-amino acid cyclodextrin derivative is a 6-deoxysulfinyl-6-thioether-amino acid cyclodextrin derivative having a structure of formula (III); and when f is 2, the 6-deoxy-6-thioether-amino acid cyclodextrin derivative is a 6-deoxysulfonyl-6-thioether-amino acid cyclodextrin derivative having a structure of formula (IV).

The formulas (II), (III) and (IV) have identical a, b, R$_1$, R$_2$, R$_3$ and M with the formula (I).

Another object of the present invention is to provide a preparation method thereof, wherein an amino acid derivative (2) is condensed with halogenated cyclodextrin (1) in presence of alkali to produce the 6-deoxy-6-thioether-amino acid cyclodextrin derivative (I), as showed in a following reaction equation.

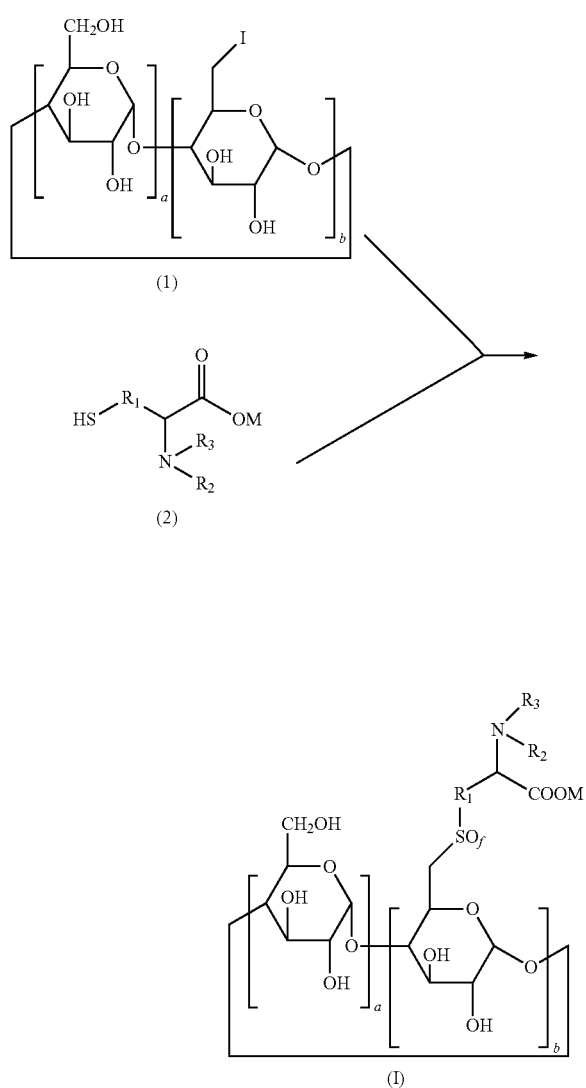

(1)

(2)

(I)

6-deoxysulfinyl-6-thioether-amino acid cyclodextrin derivative (III) is obtained via an oxidation reaction of (II); and further, 6-deoxysulfonyl-6-thioether-amino acid cyclodextrin derivative (IV) is obtained via an oxidation reaction of (III),

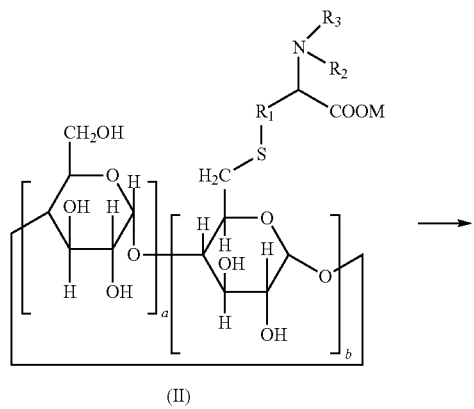

(II)

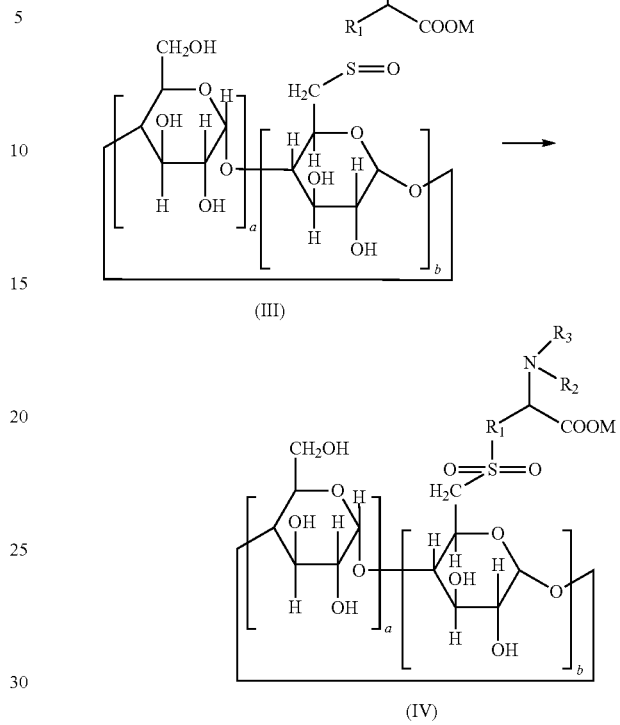

(III)

(IV)

wherein a, b, f, $R_1$, $R_2$, $R_3$ and M are as described in the formula (I).

The cyclodextrin (1) comprises α-cyclodextrin, β-cyclodextrin, γ-cyclodextrin and δ-cyclodextrin.

An oxidant of the oxidation reactions is peroxy acid salt or organic peroxide, selected from a group consisting of peroxysulfuric acid, $H_2O_2$, $KClO_4$, $H_2SO_4$, $KMnO_4$, $Na_2O_2$ and $K_2O_2$.

Another object of the present invention is to provide a method for antagonizing muscular relaxation comprising administrating a drug comprising a therapeutically effective amount of 6-deoxy-6-thioether-amino acid cyclodextrin derivative.

Compounds provided by the present invention are produced via available reactants, a stable preparation art, a high yield, low costs and environment friendliness. The compounds have an improved binding force and an improved selectivity for muscular relaxants, strong reversal and antagonism effects on the muscular relaxants and improved efficacy. More importantly, the compounds provided by the present invention are twice securer than the similar compounds according to prior arts.

These and other objectives, features, and advantages of the present invention will become apparent from the following detailed description, the accompanying drawings, and the appended claims.

DETAILED DESCRIPTION OF THE PREFERRED EMBODIMENT

One skilled in the art will understand that the embodiment of the present invention as shown in the drawings and described above is exemplary only and not intended to be limiting.

Embodiment 1

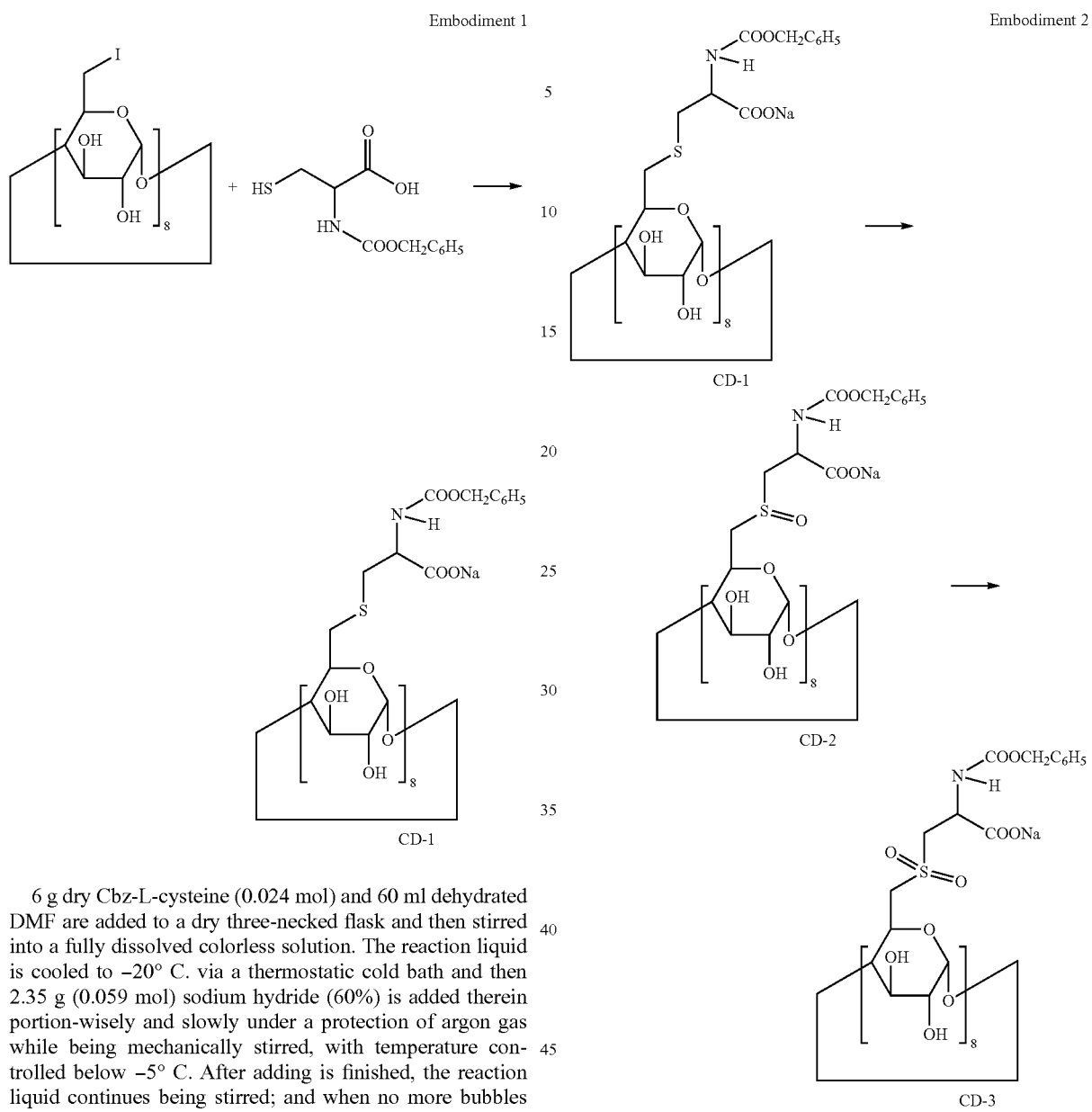

6 g dry Cbz-L-cysteine (0.024 mol) and 60 ml dehydrated DMF are added to a dry three-necked flask and then stirred into a fully dissolved colorless solution. The reaction liquid is cooled to −20° C. via a thermostatic cold bath and then 2.35 g (0.059 mol) sodium hydride (60%) is added therein portion-wisely and slowly under a protection of argon gas while being mechanically stirred, with temperature controlled below −5° C. After adding is finished, the reaction liquid continues being stirred; and when no more bubbles come out, the reaction liquid is transferred to about 5° C. and reacts for 2-3 h (until no more bubbles appears).

With a temperature of a cold bath controlled below 10° C., 2.29 g 6-per-deoxy-6-per-iodo-γ-cyclodextrin (1.05 mmol) is dissolved in DMF and then added to the solution of Cbz-L-cysteine sodium salt under the protection of argon gas while being mechanically stirred until being uniformly mixed. The mixed reaction liquid is heated to 70° C. and then reacts for 12 h. Thereafter the reaction liquid is cooled to room temperature and then filtered, wherein a filter cake is washed by acetone until no more iodide ion exists. After decompression drying, 6-per-deoxy-6-per-(N-Cbz-L-glycine methyl)thioether-γ-cyclodextrin sodium salt (CD-1) is obtained at a yield of 50%.

$^1$H nuclear magnetic resonance spectrum (NMRS) of CD-1 in heavy water (D$_2$O): δ2.69,2.44(CH$_2$,m,2H), 3.02(CH,m,H), 3.06,2.81(CH$_2$,m,2H), 3.73(2CH,m,2H), 4.19(CH,m,H), 4.7(CH,m,H), 5.03(CH,s,H), 5.05(CH$_2$,s,2H), 7.33(2CH,s,2H), 7.37(CH,s,H), 7.39(2CH,s,2H)ppm.

16.86 g CD-1 (5 mmol) suspends in 20 ml acetic acid; under stirring, 0.85 g (7.5 mmol) 30% H$_2$O$_2$ aqueous solution is added therein drop by drop; and then reaction liquid reacts at room temperature for 6 h. Thereafter, alcohol is added into the reaction liquid to precipitate solids. After recrystallizing via methanol, 6-per-deoxy-6-per-(N-Cbz-L-glycine methyl)sulfinyl-γ-cyclodextrin (CD-2) is obtained at a yield of 90%. Excessive H$_2$O$_2$ in filtrate is removed via adding sodium thiosulfate.

$^1$H NMRS of CD-2 in heavy water (D$_2$O): δ2.83,2.58 (CH$_2$,m,2H), 3.02(CH,m,H), 3.18,2.93(CH$_2$,m,2H), 3.73 (2CH,m,2H), 3.9(CH,m,H), 4.4(CH,m,H), 5.03(CH,s,H), 5.05(CH$_2$,s,2H), 7.33(2CH,s,2H), 7.37(CH,s,H), 7.39(2CH,s,2H)ppm.

16.86 g (5 mmol) CD-1 is suspended in 20 ml acetic acid; under stirring, 2.83 g (25 mmol) 30% H$_2$O$_2$ aqueous solution is added therein drop by drop; and reaction liquid is maintained 40-60° C. for reacting for 5 h. Thereafter, alcohol is added into the reaction liquid to precipitate solids. After recrystallizing via methanol, 6-per-deoxy-6-per-(N-Cbz-L-glycine methyl)sulfonyl-γ-cyclodextrin (CD-3) is obtained at a yield of 88%. Excessive $H_2O_2$ in filtrate is removed via adding sodium thiosulfate.

¹H NMRS of CD-3 in heavy water ($D_2O$): δ3.02(CH,m,H), 3.66,3.41(CH$_2$,m,2H), 4.03,3.78(CH$_2$,m,2H), 3.73 (2CH,m,2H), 3.9(CH,m,H), 4.4(CH,m,H), 5.03(CH,s,H), 5.05(CH$_2$,s,2H), 7.33(2CH,s,2H), 7.37(CH,s,H), 7.39(2CH,s,2H)ppm.

fully reacting. Thereafter, the reaction liquid is added with acetone to precipitate, filtered and dried, so as to obtain 6-per-deoxy-6-per-(α-L-glycine methyl)sulfinyl-γ-cyclodextrin (CD-5) at a yield of 91%.

¹H NMRS of CD-5 in heavy water ($D_2O$): δ2.83,2.58 (CH$_2$,m,2H), 3.02(CH,m,H), 3.18,2.93(CH$_2$,m,2H), 3.5 (CH,m,H), 3.73(2CH,m,2H), 3.9(CH,m,H), 5.03(CH,s,H) ppm.

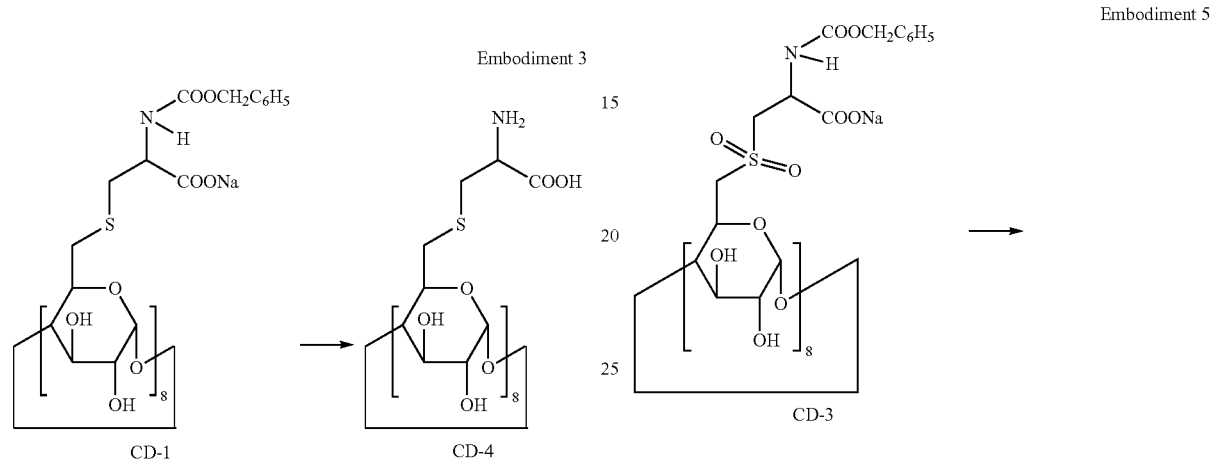

CD-1 (11.33 g, 3.36 mmol) is dissolved in glacial acetic acid (30 ml) at room temperature; under stirring, hydrogen chloride gas is injected therein. With being continuously stirred, reaction liquid is processed with thin layer chromatography (TLC) tracking until fully reacting. Then formed solid sodium chloride is filtered off. When no chloride ion is detected in mother liquor, the mother liquor is added with acetone to precipitate and then filtered. After drying, 6-per-deoxy-6-per-(α-L-glycine methyl)thioether-γ-cyclodextrin (CD-4) at a yield of 92%.

¹H NMRS of CD-4 in heavy water ($D_2O$): δ2.69,2.44 (CH$_2$,m,2H), 3.02(CH,m,H), 3.06,2.81 (CH$_2$,m,2H), 3.73 (2CH,m,2H), 3.77(CH,m,H), 4.19(CH,m,H), 5.03(CH,s,H) ppm.

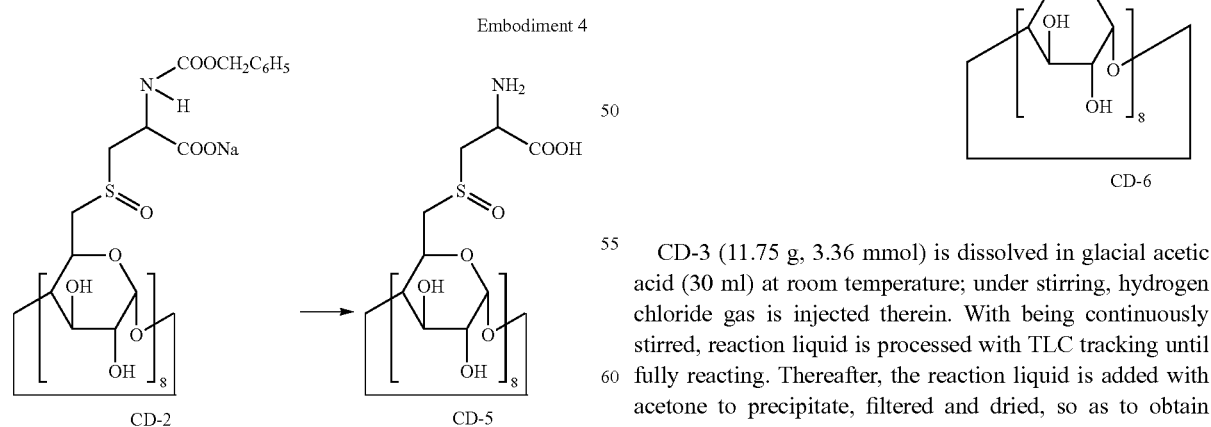

CD-2 (11.32 g, 3.36 mmol) is dissolved in glacial acetic acid (30 ml) at room temperature; under stirring, hydrogen chloride gas is injected therein. With being continuously stirred, reaction liquid is processed with TLC tracking until CD-3 (11.75 g, 3.36 mmol) is dissolved in glacial acetic acid (30 ml) at room temperature; under stirring, hydrogen chloride gas is injected therein. With being continuously stirred, reaction liquid is processed with TLC tracking until fully reacting. Thereafter, the reaction liquid is added with acetone to precipitate, filtered and dried, so as to obtain 6-per-deoxy-6-per-(α-L-glycine methyl)sulfonyl-γ-cyclodextrin (CD-6) at a yield of 87%.

¹H NMRS of CD-6 in heavy water ($D_2O$): δ3.02(CH,t,H), 3.5(CH,m,H), 3.66,3.41(CH$_2$,m,2H), 3.73(2CH,m,2H), 3.9 (CH,m,H), 4.03,3.78 (CH$_2$,m,2H), 5.03(CH,s,H)ppm.

Embodiment 6

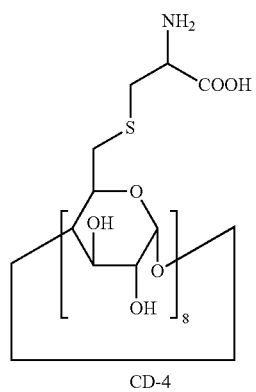

CD-4

→

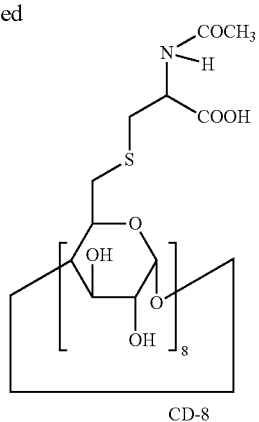

CD-8

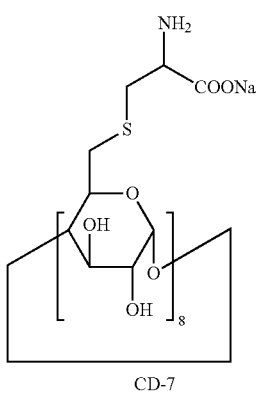

CD-7

3.42 g (1.61 mmol) CD-4 is dissolved in 2 ml water; with the solution being stirred in a cold bath, 0.064 g (1.61 mmol) sodium hydroxide aqueous solution is added therein. Then the added solution is fully stirred and monitored via spots on a plate until fully reacting. Thereafter, the reaction liquid is poured into acetone to completely precipitate solids, and then filtered while having filter cake washed with acetone. After drying, 6-per-deoxy-6-per-(α-L-glycine methyl)thio-ether-γ-cyclodextrin sodium salt (CD-7) is obtained at a yield of 98%.

¹H NMRS of CD-7 in heavy water ($D_2O$): δ2.69,2.44 (CH$_2$,m,2H), 3.02(CH,m,H), 3.06,2.81(CH$_2$,m,2H), 3.73 (3CH,m,3H), 4.19(CH,m,H), 5.03(CH,s,H)ppm.

Embodiment 7

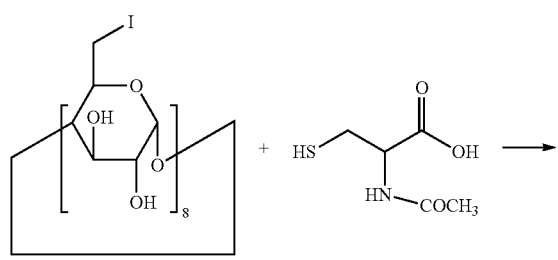

23.7 g N-acetyl cysteine (0.088 mol) and 160 ml dehydrated DMF are added to a dry three-necked flask and then stirred into a fully dissolved solution. The reaction liquid is cooled to about −10° C. via a thermostatic cold bath and then 8.81 g sodium hydride (60%) is added therein portionwisely and slowly under a protection of argon gas while being mechanically stirred, with temperature controlled below −5° C. After adding is finished, the reaction liquid continues being stirred; and when no more bubbles come out, the reaction liquid is transferred to about 5° C. and reacts until no more bubbles appears (after about 2-3 h).

With a cold bath controlled at about 5° C., a DMF solution of 8.38 g (3.85 mmol) 6-per-deoxy-6-per-iodo-γ-cyclodextrin is added to the above fully reacted reaction liquid of N-acetyl cysteine sodium salt. Under a protection of argon gas, the reaction liquid is mechanically stirred to be uniformly mixed and further stirred for 30 min. Then the reaction liquid is heated to 70° C. and reacts for 12 h. Then the reaction liquid is cooled to room temperature and filtered, wherein a filter cake is washed twice with DMF and then with acetone to remove triphenylphosphane and triphenylphosphine oxide. After a decompression drying, a crude sodium salt is obtained. The crude sodium salt is dissolved in glacial acetic acid; then with being cooled via a cold bath, the solution is injected with dry hydrogen chloride gas; and after 20 min, precipitation of white solids begins and the reaction liquid is filtered when no more white solids precipitate (about 1 h later). Then, to filtrate is gradually added dry acetone; and further the filtrate is filtered when solids precipitate out and has filter cake washed off sourness with acetone. After decompression drying, 6-per-deoxy-6-per-(N-acetyl glycine methyl)thioether-γ-cyclodextrin (CD-8) is obtained at a yield of 48%.

¹H NMRS of CD-8 in heavy water ($D_2O$): δ2.02(CH$_3$,m, 3H), 2.69,2.44(CH$_2$,m,2H), 3.02(CH,m,H), 3.06,2.81(CH$_2$, m,2H), 3.73(2CH,m,2H), 4.19(CH,m,H), 4.74(CH,m,H), 5.03(CH,s,H)ppm.

Embodiment 8

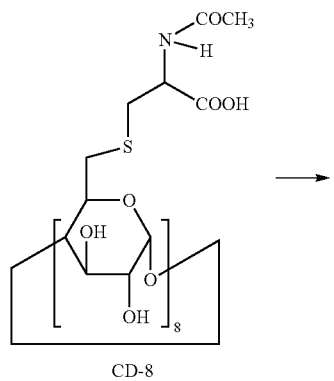

CD-8

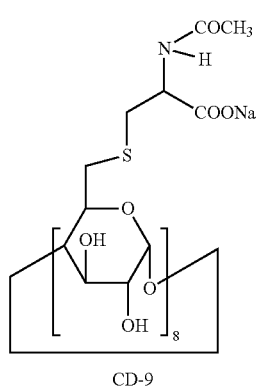

CD-9

3.96 g (1.61 mmol) CD-8 is dissolved in 10 ml water; with the solution being stirred in a cold bath, 0.064 g (1.61 mmol) sodium hydroxide aqueous solution is added therein. Then the added solution is fully stirred and monitored via spots on a plate until fully reacting. Thereafter, the reaction liquid is poured into acetone to completely precipitate solids, and then filtered while having filter cake washed with acetone. After drying, 6-per-deoxy-6-per-(N-acetyl glycine methyl) thioether-γ-cyclodextrin sodium salt (CD-9) is obtained at a yield of 96%.

$^1$H NMRS of CD-9 in heavy water (D$_2$O): δ2.02(CH$_3$,m, 3H), 2.69,2.44(CH$_2$,m,2H), 3.02(CH,m,H), 3.06,2.81(CH$_2$, m,2H), 3.73(2CH,m,2H), 4.19(CH,m,H), 4.70(CH,m,H), 5.03(CH,s,H)ppm.

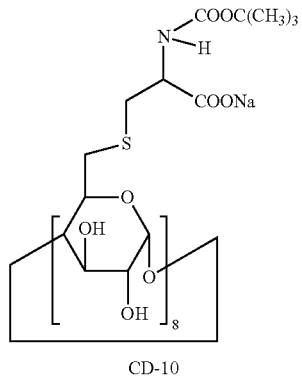

CD-10

5.31 g (0.024 mol) dry N-Boc-L-cysteine and 40 ml dehydrated DMF are added to a dry three-necked flask and then stirred into a fully dissolved solution. The reaction liquid is cooled to about −15° C. via a thermostatic cold bath and then 2.35 g (0.059 mol) sodium hydride (60%) is added therein portion-wisely and slowly under a protection of argon gas while being mechanically stirred, with temperature controlled below −5° C. After adding is finished, the reaction liquid continues being stirred; and when no more bubbles come out, the reaction liquid is transferred to about 5° C. and reacts for 2-3 h (until no more bubbles).

With a cold bath controlled below 10° C., a DMF solution of 2.29 g (1.05 mmol) 6-per-deoxy-6-per-iodo-γ-cyclodextrin is added to the above solution of N-Boc-L-cysteine sodium salt under a protection of argon gas while being mechanically stirred to being uniformly mixed. Thereafter, the added reaction liquid is further stirred for 30 min, heated to 70° C. and reacts for 12 h. Then the reaction liquid is cooled to room temperature and filtered, wherein a filter cake is washed twice with DMF and then with acetone to remove iodine ion. After a decompression drying, 6-per-deoxy-6-per-(N-Boc-L-glycine methyl)thioether-γ-cyclodextrin sodium salt (CD-10) is obtained at a yield of 46%.

$^1$H NMRS of CD-10 in heavy water (D$_2$O): δ1.42(3CH$_3$, m,9H), 2.69,2.44(CH$_2$,m,2H), 3.02(CH,m,H), 3.06,2.81 (CH$_2$,m,2H), 3.5(CH,m,H), 3.73(2CH,m,2H), 4.19(CH,m, H), 4.7(CH,m,H), 5.03(CH,s,H)ppm.

Embodiment 9

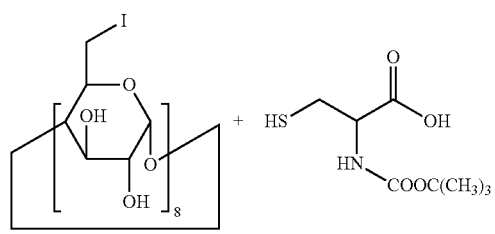

Embodiment 10

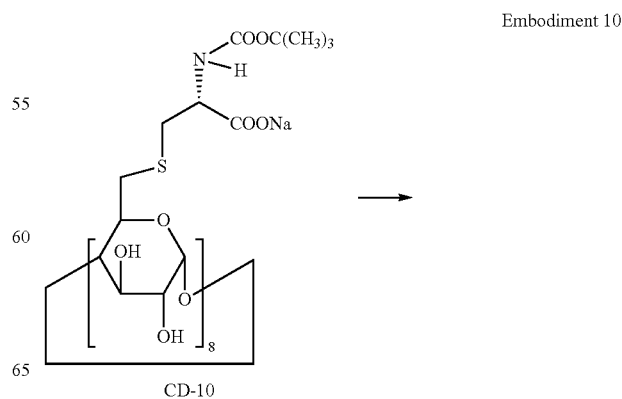

CD-10

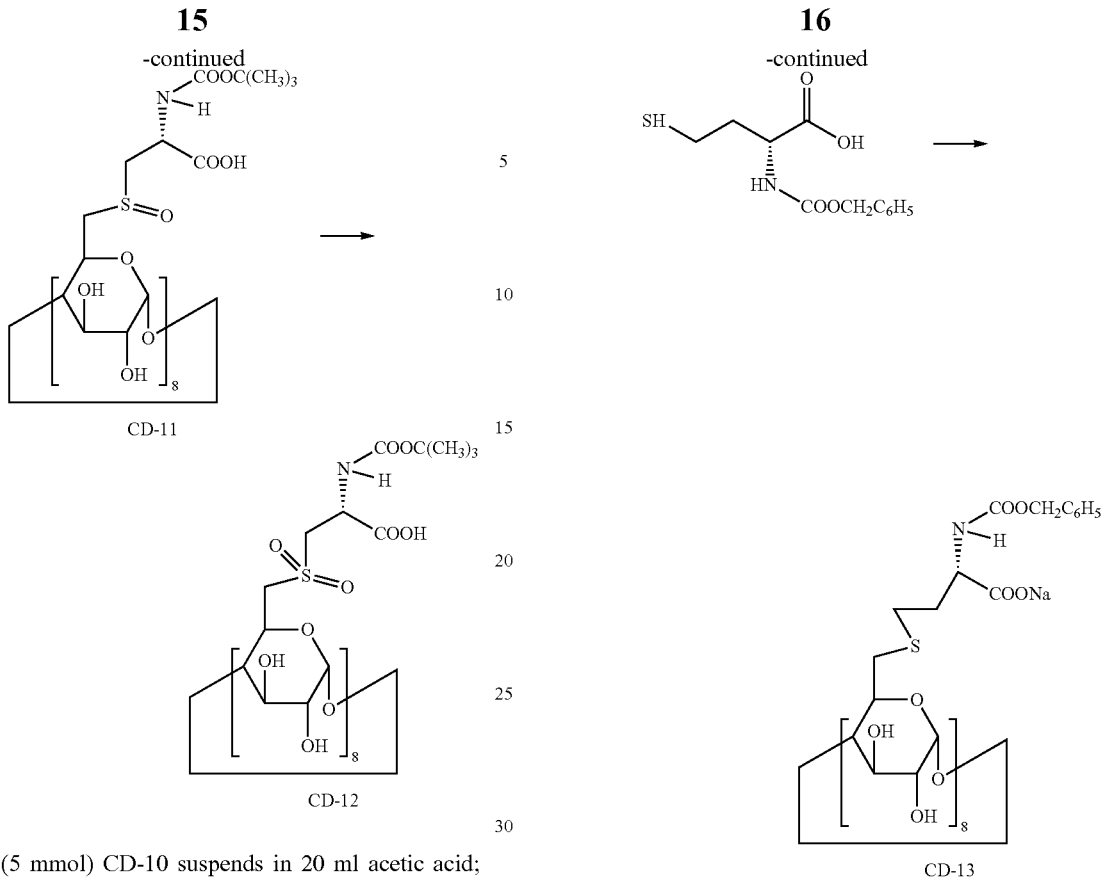

15.5 g (5 mmol) CD-10 suspends in 20 ml acetic acid; under stirring, 0.85 g (7.5 mmol) 30% $H_2O_2$ aqueous solution is added therein drop by drop; and then reaction liquid reacts at room temperature for 6 h. Alcohol is added to the reaction liquid to precipitate. After recrystallizing via methanol, 6-per-deoxy-6-per-(N-Boc-L-glycine methyl)sulfinyl-γ-cyclodextrin (CD-11) is obtained at a yield of 90.2%. Excessive $H_2O_2$ in filtrate is removed via adding sodium thiosulfate.

$^1$H NMRS of CD-11 in heavy water ($D_2O$): δ1.42(3$CH_3$, m,9H), 2.83,2.58($CH_2$,m,2H), 3.02(CH,m,H), 3.18,2.93 ($CH_2$,m,2H), 3.73(2CH,m,2H), 3.9(CH,m,H), 4.4(CH,m,H), 5.03(CH,s,H)ppm.

15.5 g (5 mmol) CD-10 suspends in 20 ml acetic acid; under stirring, 2.83 g (25 mmol) 30% $H_2O_2$ aqueous solution is added therein drop by drop; and then reaction liquid reacts at 40-60° C. for 5 h. Alcohol is added to the reaction liquid to precipitate. After recrystallizing via methanol, 6-per-deoxy-6-per-(N-Boc-L-glycine methyl)sulfonyl-γ-cyclodextrin (CD-12) is obtained at a yield of 91.3%. Excessive $H_2O_2$ in filtrate is removed via adding sodium thiosulfate.

$^1$H NMRS of CD-12 in heavy water ($D_2O$): δ1.42(3$CH_3$, m,9H), 3.02(CH,m,H), 3.66,3.41($CH_2$,m,2H), 4.03,3.78 ($CH_2$,m,2H), 3.73(2CH,m,2H), 3.9(CH,m,H), 4.4(CH,m,H), 5.03(CH,s,H)ppm.

Embodiment 11

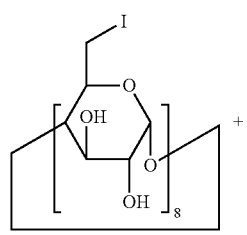

24.93 g (0.088 mol) Boc-L-homocysteine and 160 ml dehydrated DMF are added to a dry three-necked flask and stirred until solids are fully dissolved. The reaction liquid is cooled to about −10° C. via a thermostatic cold bath and 8.81 g (60%) sodium hydride is added therein portion-wisely and slowly under a protection of argon gas while being mechanically stirred, with temperature controlled below −5° C. After adding is finished, the reaction liquid continues being stirred; and when no more bubbles come out, the reaction liquid is transferred to about 5° C. and reacts until no more bubbles come out (after about 2-3 h), wherein extra DMF is supplemented into the reaction liquid when the reaction liquid become sticky in the process of stirring.

With a cold bath controlled at about 5° C., a DMF solution of 8.38 g (3.85 mmol) 6-per-deoxy-6-per-iodo-γ-cyclodextrin is added to the above fully reacted reaction liquid of Boc-L-monocysteine sodium salt; and products wholly enter the reaction liquid by washing a reaction bottle with 30 ml DMF. Under a protection of argon gas, after being mechanically stirred to being uniformly mixed, the reaction liquid continues being stirred for 30 min. Thereafter, the reaction liquid is heated to 70° C. and reacts for 12 h. Then the reaction liquid is cooled to room temperature and filtered, wherein a filter cake is washed twice with DMF and then with acetone to remove triphenylphosphane and triphenylphosphine oxide. After a decompression drying, 6-per-deoxy-6-per-(N-Boc-L-glycine ethyl)thioether-γ-cyclodextrin sodium salt (CD-13) is obtained at a yield of 43%.

$^1$H NMRS of CD-13 in heavy water ($D_2O$): δ2.15($CH_2$, m,2H), 2.44($CH_2$,m,2H), 2.69,2.44($CH_2$,m,2H), 3.02(CH, m,H), 4.19(CH,m,H), 3.73(2CH,m,2H), 4.42(CH,m,H), 5.03(CH,s,H), 5.05(CH,s,H), 7.33(2CH,m,2H), 7.37(CH,m, H), 7.39(2CH,m,2H ppm.

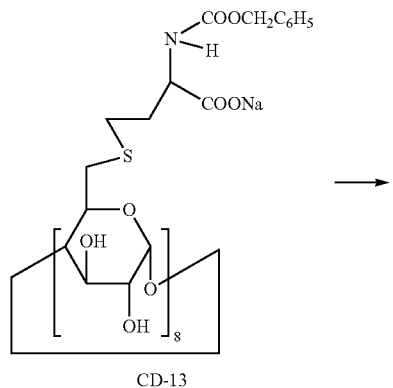

CD-13

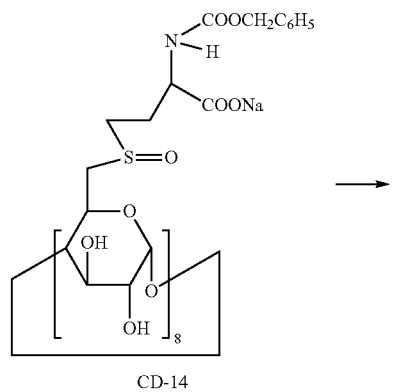

CD-14

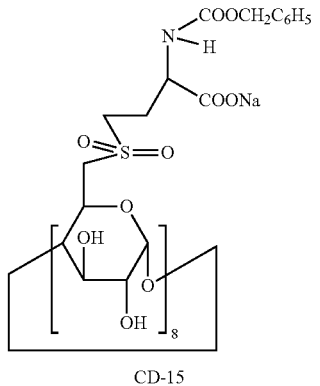

CD-15

15.24 g (5 mmol) CD-13 suspends in 20 ml acetic acid; under stirring, 0.85 g (7.5 mmol) 30% $H_2O_2$ aqueous solution is added therein drop by drop; and then reaction liquid reacts at room temperature for 6 h. Alcohol is added to the reaction liquid to precipitate. After recrystallizing via methanol, 6-per-deoxy-6-per-(N-Boc-L-glycine ethyl)sulfinyl-γ-cyclodextrin (CD-14) is obtained at a yield of 87.6%. Excessive $H_2O_2$ in filtrate is removed via adding sodium thiosulfate.

$^1$H NMRS of CD-14 in heavy water ($D_2O$): δ2.12($CH_2$, m,2H), 2.57($CH_2$,m,2H), 2.83,2.58($CH_2$,m,2H), 3.02(CH, m,H), 3.9(CH,m,H), 3.73(2CH,m,2H), 4.42(CH,m,H), 5.03 (CH,s,H), 5.05(CH,s,H), 7.33(2CH,m,2H), 7.37(CH,m,H), 7.39(2CH,m,2H)ppm.

15.24 g (5 mmol) CD-13 suspends in 20 ml acetic acid; under stirring, 2.83 g (25 mmol) 30% $H_2O_2$ aqueous solution is added therein drop by drop; and then reaction liquid reacts at 40-60° C. for 5 h. Alcohol is added to the reaction liquid to precipitate. After recrystallizing via methanol, 6-per-deoxy-6-per-(N-Boc-L-glycine ethyl)sulfonyl-γ-cyclodextrin (CD-15) is obtained at a yield of 84.3%. Excessive $H_2O_2$ in filtrate is removed via adding sodium thiosulfate.

$^1$H NMRS of CD-15 in heavy water ($D_2O$): δ2.34($CH_2$, m,2H), 3.02(CH,m,H), 3.41($CH_2$,m,2H), 3.66,3.41($CH_2$,m, 2H), 3.9(CH,m,H), 3.73(2CH,m,2H), 4.42(CH,m,H), 5.03 (CH,s,H), 5.05(CH,s,H), 7.33(2CH,m,2H), 7.37(CH,m,H), 7.39(2CH,m,2H)ppm.

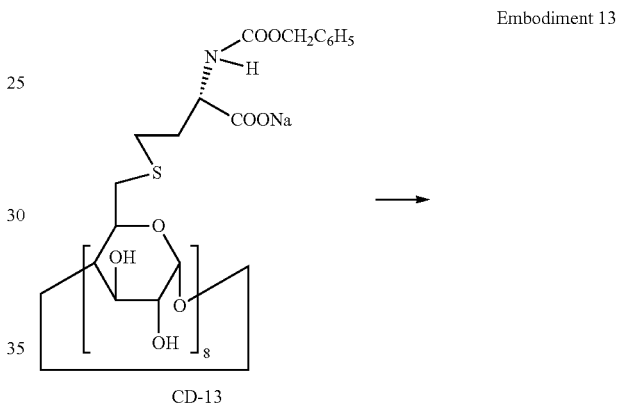

CD-13

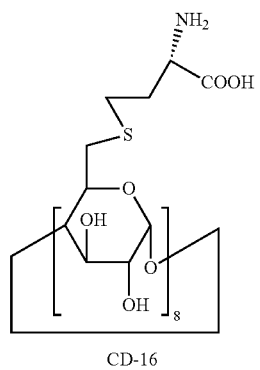

CD-16

CD-13 (10.62 g, 3.36 mmol) is dissolved in glacial acetic acid (30 ml) at room temperature; under stirring, hydrogen chloride gas is injected therein. With being continuously stirred, reaction liquid is processed with TLC tracking until fully reacting. Then formed solid sodium chloride is filtered off. When no chloride ion is detected in mother liquor, the mother liquor is added with acetone to precipitate and then filtered. After drying, 6-per-deoxy-6-per-(α-L-glycine ethyl) thioether-γ-cyclodextrin (CD-16) at a yield of 89.2%.

$^1$H NMRS of CD-16 in heavy water ($D_2O$): δ2.15($CH_2$, m,2H), 2.44($CH_2$,m,2H), 2.69,2.44($CH_2$,m,2H), 3.02(CH, m,H), 3.49(CH,m,H), 3.73(2CH,m,2H), 4.19(CH,m,H), 5.03(CH,s,H)ppm.

Embodiment 14

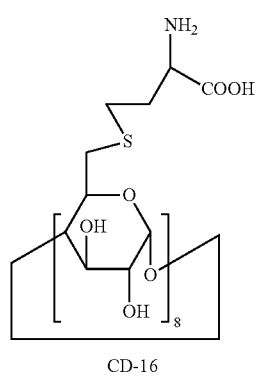

CD-16

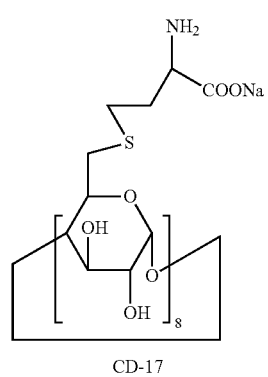

CD-17

3.54 g (1.61 mmol) CD-16 is dissolved in 2 ml water; with the solution being stirred in a cold bath, 0.064 g (1.61 mmol) sodium hydroxide aqueous solution is added therein. Then the added solution is fully stirred and monitored via spots on a plate until fully reacting. Thereafter, the reaction liquid is poured into acetone to completely precipitate solids, and then filtered while having a filter cake washed with acetone. After drying, 6-per-deoxy-6-per-(α-L-amino acid ethyl) thioether-γ-cyclodextrin sodium salt (CD-17) is obtained at a yield of 94%.

'H NMRS of CD-17 in heavy water (D$_2$O): δ2.15(CH$_2$, m,2H), 2.44(CH$_2$,m,2H), 2.69,2.44(CH$_2$,m,2H), 3.02(CH, m,H), 3.45(CH,m,H), 3.73(2CH,m,2H), 4.19(CH,m,H), 5.03(CH,s,H)ppm.

Embodiment 15

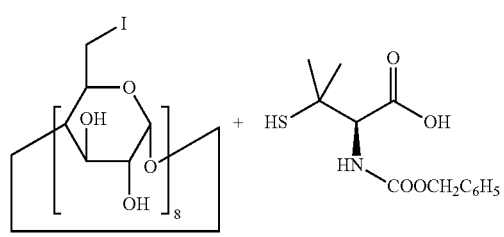

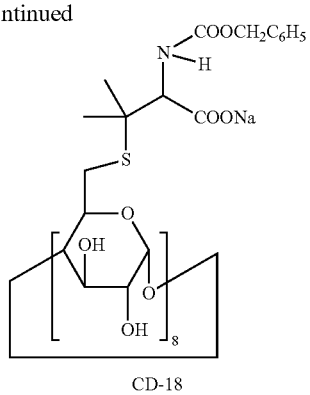

CD-18

24.93 g (0.088 mol) Boc-D-penicillamine and 160 ml dehydrated DMF are added to a dry three-necked flask and stirred until solids are fully dissolved. The reaction liquid is cooled to about −10° C. via a thermostatic cold bath and 8.81 g (60%) sodium hydride is added therein portion-wisely and slowly under a protection of argon gas while being mechanically stirred, with temperature controlled below −5° C. After adding is finished, the reaction liquid continues being stirred; and when no more bubbles come out, the reaction liquid is transferred to about 5° C. and reacts until no more bubbles come out (after about 2-3 h), wherein extra DMF is supplemented into the reaction liquid when the reaction liquid become sticky in the process of stirring.

With a cold bath controlled at about 5° C., a DMF solution of 8.38 g (3.85 mmol) 6-per-deoxy-6-per-iodo-γ-cyclodextrin is added to the above fully reacted reaction liquid of Boc-D-penicillamine sodium salt; and products wholly enter the reaction liquid by washing a reaction bottle with 30 ml DMF. Under a protection of argon gas, after being mechanically stirred to being uniformly mixed, the reaction liquid continues being stirred for 30 min. Thereafter, the reaction liquid is heated to 70° C. and reacts for 12 h. Then the reaction liquid is cooled to room temperature and filtered, wherein a filter cake is washed twice with DMF and then with acetone to remove triphenylphosphane and triphenylphosphine oxide. After a decompression drying, 6-per-deoxy-6-per-(N-Boc-D-glycine dimethyl)thioether-γ-cyclodextrin sodium salt (CD-18) is obtained at a yield of 44%.

'H NMRS of CD-18 in heavy water (D$_2$O): δ1.35(2CH$_3$, m,6H), 2.69,2.44(CH$_2$,m,2H), 3.02(CH,m,H), 3.73(2CH,m, 2H), 4.19(CH,m,H), 4.68(CH,m,H), 5.03(CH,s,H), 5.05 (CH,s,H), 7.33(2CH,m,2H), 7.37(CH,m,H), 7.39(2CH,m, 2H)ppm.

Embodiment 16

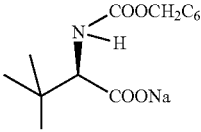

CD-18

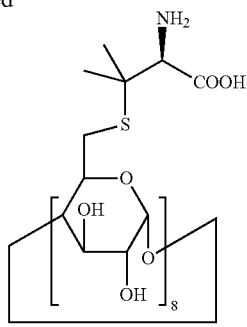

CD-19

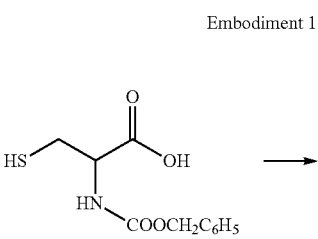

Embodiment 18

CD-18 (12.51 g, 3.36 mmol) is dissolved in glacial acetic acid (30 ml) at room temperature; under stirring, hydrogen chloride gas is injected therein. With being continuously stirred, reaction liquid is processed with TLC tracking until fully reacting. Then formed solid sodium chloride is filtered off. When no chloride ion is detected in mother liquor, the mother liquor is added with acetone to precipitate and then filtered. After drying, 6-per-deoxy-6-per-(α-D-amino acid dimethyl)sulfinyl-γ-cyclodextrin (CD-19) at a yield of 82.7%.

¹H NMRS of CD-19 in heavy water (D₂O): δ1.35(2CH₃, s,6H), 2.69,2.44(CH₂,m,2H), 3.02(CH,m,H), 3.73(2CH,m, 2H), 3.75(CH,m,H), 4.19(CH,m,H), 5.03(CH,s,H)ppm.

Embodiment 17

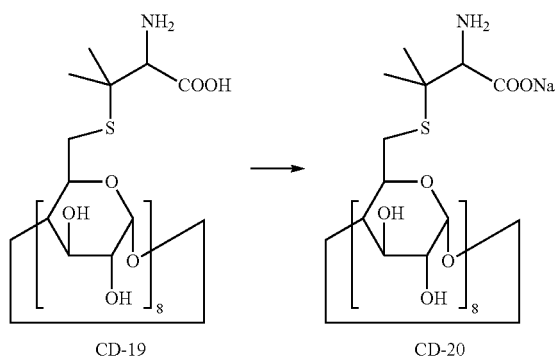

CD-19    CD-20

3.79 g (1.61 mmol) CD-19 is dissolved in 2 ml water; with the solution being stirred in a cold bath, 0.064 g (1.61 mmol) sodium hydroxide aqueous solution is added therein. Then the added solution is fully stirred and monitored via spots on a plate until fully reacting. Thereafter, the reaction liquid is poured into acetone to completely precipitate solids, and then filtered while having a filter cake washed with acetone. After drying, 6-per-deoxy-6-per-(α-D-amino acid dimethyl) sulfinyl-γ-cyclodextrin sodium salt (CD-20) is obtained at a yield of 93.5%.

¹H NMRS of CD-20 in heavy water (D₂O): δ1.35(2CH₃, s,6H), 2.69,2.44(CH₂,m,2H), 3.02(CH,m,H), 3.71(CH,m, H), 3.73(2CH,m,2H), 4.19(CH,m,H), 5.03(CH,s,H)ppm.

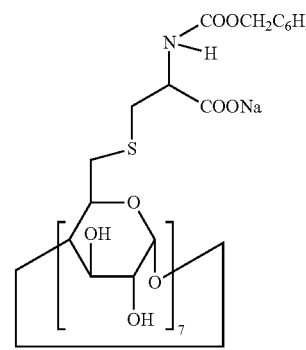

CD-21

6 g (0.024 mol) dehydrated Boc-L-cysteine and 60 ml dehydrated DMF are added to a dry three-necked flask and then stirred into a fully dissolved colorless solution. The reaction liquid is cooled to −20° C. via a thermostatic cold bath and then 2.35 g (0.059 mol) sodium hydride (60%) is added therein portion-wisely and slowly under a protection of argon gas while being mechanically stirred, with temperature controlled below −5° C. After adding is finished, the reaction liquid continues being stirred; and when no more bubbles come out, the reaction liquid is transferred to about 5° C. and reacts for 2-3 h (until no more bubbles).

With a cold bath controlled below 10° C., a DMF solution of 2 g (1.05 mmol) 6-per-deoxy-6-per-iodo-β-cyclodextrin is added to the above solution of Boc-L-cysteine sodium salt under a protection of argon gas while being mechanically stirred to being uniformly mixed. Thereafter, the reaction liquid is heated to 70° C. and reacts for 12 h. Then the reaction liquid is cooled to room temperature and filtered, wherein a filter cake is washed with acetone to remove iodine ion. After a decompression drying, 6-per-deoxy-6-per-(N-Boc-L-glycine methyl)thioether-β-cyclodextrin sodium salt (CD-21) is obtained at a yield of 56%.

¹H NMRS of CD-21 in heavy water (D₂O): δ2.69,2.44 (CH₂,m,2H), 3.02(CH,m,H), 3.06,2.81(CH₂,m,2H), 3.73 (2CH,m,2H), 4.19(CH,m,H), 4.7(CH,m,H), 5.03(CH,s,H), 5.05(CH₂,s,2H), 7.33(2CH,s,2H), 7.37(CH,s,H), 7.39(2CH, s,2H)ppm.

Embodiment 19

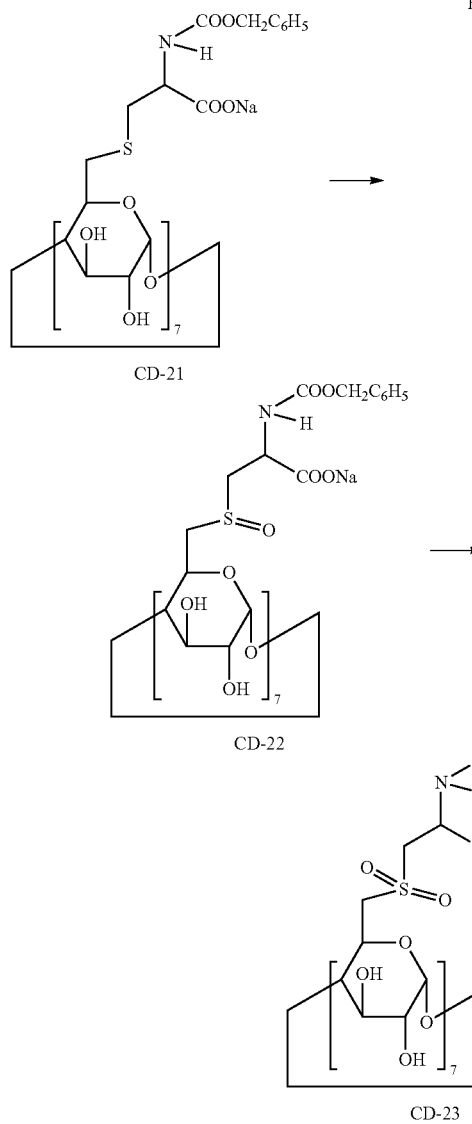

14.75 g (5 mmol) CD-21 suspends in 20 ml acetic acid; under stirring, 0.85 g (7.5 mmol) 30% $H_2O_2$ aqueous solution is added therein drop by drop; and then reaction liquid reacts at room temperature for 6 h. Alcohol is added to the reaction liquid to precipitate. After recrystallizing via methanol, 6-per-deoxy-6-per-(N-Boc-L-glycine methyl)sulfinyl-β-cyclodextrin (CD-22) is obtained at a yield of 83.5%. Excessive $H_2O_2$ in filtrate is removed via adding sodium thiosulfate.

$^1$H NMRS of CD-22 in heavy water ($D_2O$): δ2.83,2.58 (CH$_2$,m,2H), 3.02(CH,m,H), 3.18,2.93(CH$_2$,m,2H), 3.73 (2CH,m,2H), 3.9(CH,m,H), 4.4(CH,m,H), 5.03(CH,s,H), 5.05(CH$_2$,s,2H), 7.33(2CH,s,2H), 7.37(CH,s,H), 7.39(2CH, s,2H)ppm.

14.75 g (5 mmol) CD-21 suspends in 20 ml acetic acid; under stirring, 2.83 g (25 mmol) 30% $H_2O_2$ aqueous solution is added therein drop by drop; and then reaction liquid reacts at 40-60° C. for 5 h. Alcohol is added to the reaction liquid to precipitate. After recrystallizing via methanol, 6-per-deoxy-6-per-(N-Boc-L-glycine methyl)sulfonyl-β-cyclodextrin (CD-23) is obtained at a yield of 81.6%. Excessive $H_2O_2$ in filtrate is removed via adding sodium thiosulfate.

$^1$H NMRS of CD-23 in heavy water ($D_2O$): δ3.02(CH, m, H), 3.66,3.41(CH$_2$,m,2H), 4.03,3.78(CH$_2$,m,2H), 3.73 (2CH,m,2H), 3.9(CH,m,H), 4.4(CH,m,H), 5.03(CH,s,H), 5.05(CH$_2$,s,2H), 7.33(2CH,s,2H), 7.37(CH,s,H), 7.39(2CH, s,2H)ppm.

Embodiment 20

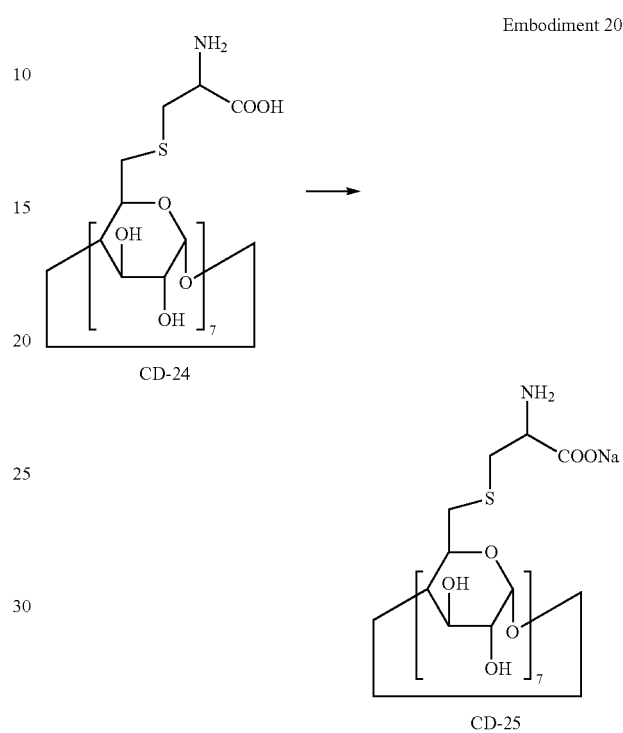

2.99 g (1.61 mmol) 6-per-deoxy-6-per-(α-D-glycine methyl)thioether-β-cyclodextrin (CD-23) is dissolved in 2 ml water; with the solution being stirred in a cold bath, 0.064 g (1.61 mmol) sodium hydroxide aqueous solution is added therein. Then the added solution is fully stirred and monitored via spots on a plate until fully reacting. Thereafter, the reaction liquid is poured into acetone to completely precipitate solids, and then filtered while having a filter cake washed with acetone. After drying, 6-per-deoxy-6-per-(α-D-glycine methyl)thioether-β-cyclodextrin sodium salt (CD-25) is obtained at a yield of 98%.

$^1$H NMRS of CD-25 in heavy water ($D_2O$): δ2.69,2.44 (CH$_2$,m,2H), 3.02(CH,m,H), 3.06,2.81(CH$_2$,m,2H), 3.73 (3CH,m,3H), 4.19(CH,m,H), 5.03(CH,s,H)ppm.

Embodiment 21

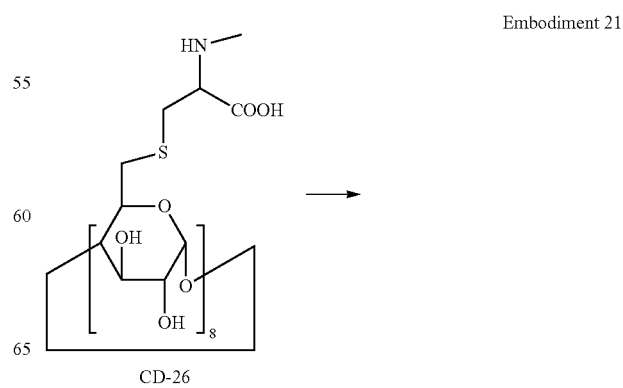

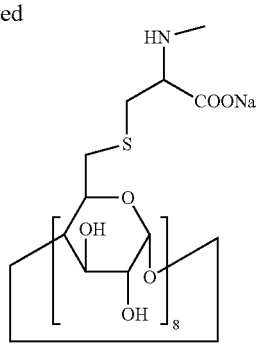

CD-27

3.6 g (1.61 mmol) 6-per-deoxy-6-per-(N-methyl-D-cysteine)thioether-β-cyclodextrin (CD-26) is dissolved in 2 ml water; with the solution being stirred in a cold bath, 0.064 g (1.61 mmol) sodium hydroxide aqueous solution is added therein. Then the added solution is fully stirred and monitored via spots on a plate until fully reacting. Thereafter, the reaction liquid is poured into acetone to completely precipitate solids, and then filtered while having a filter cake washed with acetone. After drying, 6-per-deoxy-6-per-(N-methyl-D-cysteine)thioether-β-cyclodextrin sodium salt (CD-27) is obtained at a yield of 97%.

$^1$H NMRS of CD-27 in heavy water (D$_2$O): δ2.47(CH$_3$, m,3H), 2.69,2.44(CH$_2$,m,2H), 2.91,2.66(CH$_2$,m,2H), 3.02 (CH,m,H), 3.73(3CH,m,3H), 4.19(CH,m,H), 5.03(CH,s,H) ppm.

Embodiment 22

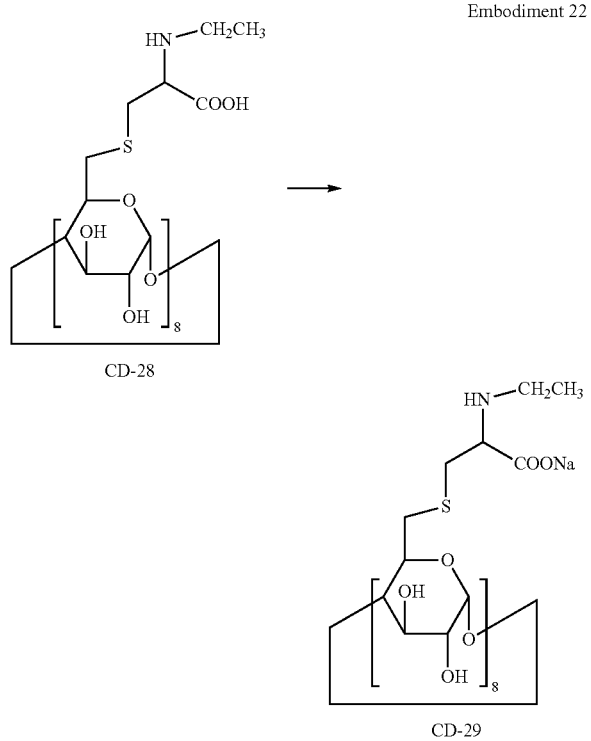

CD-28

CD-29

3.78 g (1.61 mmol) 6-per-deoxy-6-per-(N-ethyl-D-cysteine)thioether-β-cyclodextrin (CD-28) is dissolved in 2 ml water; with the solution being stirred in a cold bath, 0.064 g (1.61 mmol) sodium hydroxide aqueous solution is added therein. Then the added solution is fully stirred and monitored via spots on a plate until fully reacting. Thereafter, the reaction liquid is poured into acetone to completely precipitate solids, and then filtered while having a filter cake washed with acetone. After drying, 6-per-deoxy-6-per-(N-ethyl-D-cysteine)thioether-β-cyclodextrin sodium salt (CD-29) is obtained at a yield of 94.3%.

$^1$H NMRS of CD-29 in heavy water (D$_2$O): δ1.00(CH$_3$, m,3H), 2.59(CH$_2$,m,2H), 2.69,2.44(CH$_2$,m,2H), 2.91,2.66 (CH$_2$,m,2H), 3.02(CH,m,H), 3.73(3CH,m,3H), 4.19(CH,m,H), 5.03(CH,s,H)ppm.

Embodiment 23

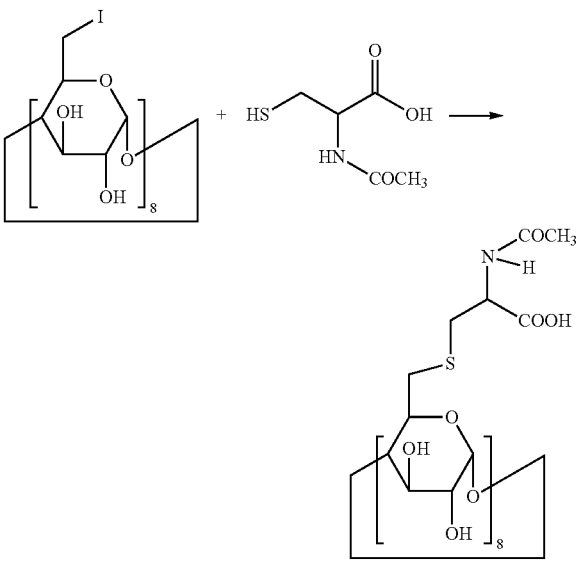

CD-30

23.7 g (0.088 mol) N-acetyl-D-cysteine and 160 ml dry DMF are added to a dry three-necked flask and then stirred into a fully dissolved solution. The reaction liquid is cooled to −10° C. via a thermostatic cold bath and then 8.81 g (60%) sodium hydride is added therein portion-wisely and slowly under a protection of argon gas while being mechanically stirred, with temperature controlled below −5° C. After adding is finished, the reaction liquid continues being stirred; and when no more bubbles come out, the reaction liquid is transferred to about 5° C. and reacts until no more bubbles come out (after about 2-3 h).

With a cold bath controlled at about 5° C., a DMF solution of 8.38 g (3.85 mmol) 6-per-deoxy-6-per-iodo-γ-cyclodextrin is added to the above fully reacted reaction liquid of N-acetyl-D-cysteine sodium salt. Under a protection of argon gas, the reaction liquid is mechanically stirred to be uniformly mixed and further stirred for 30 min. Then the reaction liquid is heated to 70° C. and reacts for 12 h. Then the reaction liquid is cooled to room temperature and filtered, wherein a filter cake is washed twice with DMF and then with acetone to remove triphenylphosphane and triphenylphosphine oxide. After a decompression drying, a crude sodium salt is obtained. The crude sodium salt is dissolved in glacial acetic acid; then with being cooled via a cold bath, the solution is injected with dry hydrogen chloride gas; and after 20 min, precipitation of white solids begins and the reaction liquid is filtered when no more white solids precipitate (after about 1 h). Then, to filtrate is gradually added dry acetone; and further the filtrate is filtered when solids precipitate out and has a filter cake washed off sourness with acetone. After decompression drying, 6-per-deoxy-6-per-(N-acetyl-D-glycine methyl)thioether-γ-cyclodextrin (CD-30) is obtained at a yield of 51%.

$^1$H NMRS of CD-30 in heavy water (D$_2$O): δ2.02(CH$_3$, m,3H), 2.69,2.44(CH$_2$,m,2H), 3.02(CH,m,H), 3.06,2.81 (CH$_2$,m,2H), 3.73(2CH,m,2H), 4.19(CH,m,H), 4.74(CH,m, H), 5.03(CH,s,H)ppm.

Embodiment 24

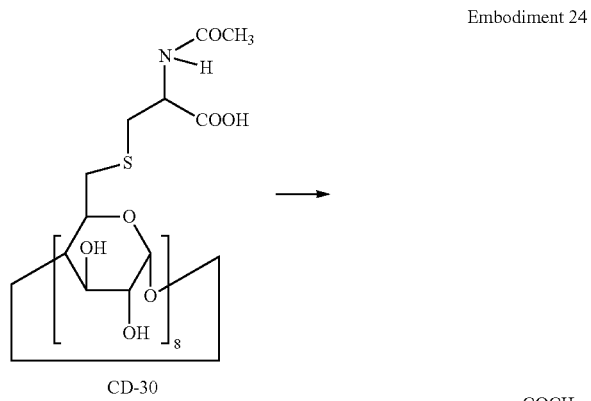

CD-30

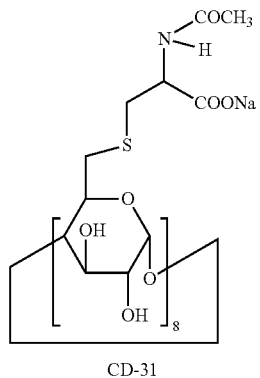

CD-31

3.96 g (1.61 mmol) CD-30 is dissolved in 10 ml water; with the solution being stirred in a cold bath, 0.064 g (1.61 mmol) sodium hydroxide aqueous solution is added therein. Then the added solution is fully stirred and monitored via spots on a plate until fully reacting. Thereafter, the reaction liquid is poured into acetone to completely precipitate solids, and then filtered while having a filter cake washed with acetone. After drying, 6-per-deoxy-6-per-(α-D-glycine methyl)thioether-γ-cyclodextrin sodium salt (CD-31) is obtained at a yield of 96.4%.

$^1$H NMRS of CD-31 in heavy water (D$_2$O): δ2.02(CH$_3$, m,3H), 2.69,2.44(CH$_2$,m,2H), 3.02(CH,m,H), 3.06,2.81 (CH$_2$,m,2H), 3.73(2CH,m,2H), 4.19(CH,m,H), 4.70(CH,m, H), 5.03(CH,s,H) ppm.

Embodiment 25

Guinea pigs are injected with atropine 30 min before operation. After pentobarbital sodium anesthesia in the abdominal cavity, the Guinea pigs are fixed on rat boards and connected to small animal ventilators after endotracheal intubation. Stimulating electrodes of a muscular relaxation monitor, TOF-Watch SX, are respectively connected to left post-femur and post-tibialis subcutis of the Guinea pig. Self-made tools are used to fix the left tibialis on a small platform while permitting the left hind paw to be able to move freely. A sensor is fixed on a palm surface of a left hind leg of the Guinea pig and a probe of skin temperature is fixed on a palm surface of a left front leg of the Guinea pig. Adjusting 4 train-of-four stimulations (TOF, frequency of 2 Hz, pulse width of 0.2 ms, and inter-train interval of 15 s), TOF stimulating voltage of 5 mA; 5 min after sensitivity adjustment stabilizes T1, intravenous injecting 0.16 m/kg (twice ED90 dose) rocuronium bromide (Organon Company of Netherlands, 50 mg/5 ml).

When T4/T1(TOFR) disappears and T1 decreases more than 80%, compounds of the present invention (2 mg/kg) are given. Measurements comprise:

(1) time for TOFR to recover from 0 to 50% and to 75%; and (2) time of T1 to recover to 25%, to 50% and to 75%. Table 1 shows results.

TABLE 1

| treatment group | T1 recovering to 25%/time* | T1 recovering to 50%/time | T1 recovering to 75%/time | TOF recovering to 50%/time | TOF recovering to 75%/time |
|---|---|---|---|---|---|
| model group | 21.00 | 25.30 | 33.00 | 24.05 | 27.10 |
| CD-27 | 8.25 | 11.25 | 16.00 | 8.25 | 10.75 |
| CD-26 | 7.75 | 12.25 | 16.00 | 8.00 | 11.75 |
| CD-28 | 8.25 | 12.25 | 15.00 | 12.75 | 16.25 |
| CD-29 | 6.75 | 8.50 | 9.25 | 6.50 | 8.25 |
| CD-5 | 3.50 | 4.25 | 8.25 | 4.75 | 7.25 |
| CD-16 | 2.25 | 3.50 | 8.50 | 3.50 | 5.75 |
| CD-4 | 2.25 | 2.00 | 4.50 | 2.25 | 3.75 |
| CD-7 | 1.25 | 1.50 | 2.75 | 1.25 | 1.50 |
| CD-8 | 2.25 | 2.75 | 4.25 | 2.50 | 3.50 |
| CD-9 | 1.25 | 1.75 | 2.25 | 1.50 | 3.25 |
| CD-17 | 3.00 | 5.25 | 7.75 | 3.00 | 6.25 |

*All the recovering times are counted as minutes from a time point when TOF disappears and T1 decreases more than 80%, which indicates that the compounds of the present invention have obvious antagonism against muscular relaxation induced by rocuronium bromide, wherein CD-7 and CD-9 effect antagonizing the muscular relaxation most rapidly and have most obvious effects.

Embodiment 26

Male small mice are processed with intravenous injection with compounds of the present invention at the tails. Table 2 shows results of observing toxic reactions.

TABLE 2

| group | concentration | dose | result description |
|---|---|---|---|
| CD-7 | 200 mg/ml | 4000 mg/kg | normal |
| CD-9 | 200 mg/ml | 4000 mg/kg | normal |
| CD-17 | 200 mg/ml | 4000 mg/kg | normal |
| CD-20 | 200 mg/ml | 4000 mg/kg | normal |
| CD-25 | 200 mg/ml | 4000 mg/kg | normal |
| CD-27 | 200 mg/ml | 4000 mg/kg | normal |
| CD-29 | 200 mg/ml | 4000 mg/kg | normal |

According to reports, a maximal safe dose of Bridion, disclosed in CN1402737, for small mice is 2000 mg/kg; however, the small mice are still normal when given the 4000 mg/kg compound of the present invention, such as CD-7, CD-9, CD-17, CD-20, CD-25, CD-27 and CD-29, which indicates that a safe dose of the compounds of the present invention is doubled and the compounds of the present invention have improved pharmaceutical security.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A method for antagonizing muscular relaxation induced by a muscular relaxant, the method comprising administrating a therapeutically effective amount of a 6-deoxy-6-thioether amino acid cyclodextrin derivative having a structure of formula (I),

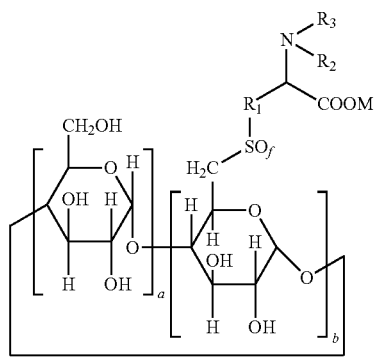

wherein a is 0;
b is 8;
f is 0;
$R_1$ is $CH_2$; $R_2$ is —H; $R_3$ is an acetyl group; and
M is —H, $NH_4$ or alkali metal ion wherein the muscular relaxant is a neuromuscular blocking drug.

2. The method of claim 1, wherein M is Na.

3. The method of claim 1, wherein the muscular relaxant is pancuronium bromide.

4. The method of claim 1, wherein the muscular relaxant is pipecuronium bromide.

5. The method of claim 1, wherein the muscular relaxant is dacuronium bromide.

6. The method of claim 1, wherein the muscular relaxant is quindonium bromide.

7. The method of claim 1, wherein the muscular relaxant is rocuronium bromide.

8. The method of claim 1, wherein the muscular relaxant is vecuronim bromide.

* * * * *

UNITED STATES PATENT AND TRADEMARK OFFICE
CERTIFICATE OF CORRECTION

PATENT NO. : 10,669,352 B2
APPLICATION NO. : 16/028902
DATED : June 2, 2020
INVENTOR(S) : Youmao Qi It is certified that error appears in the above-identified patent and that said Letters Patent is hereby corrected as shown below:

On the Title Page

Item (57), Column 2 (Abstract): Delete "rage" and insert -- range --, therefor.

In the Claims

Column 30, Line 6: In Claim 1, after "ion" insert -- , --.

Column 30, Line 23: In Claim 8, delete "vecuronim" and insert -- vecuronium --, therefor.

Signed and Sealed this
Twenty-eighth Day of July, 2020

Andrei Iancu
*Director of the United States Patent and Trademark Office*